Aug. 29, 1961 R. S. MOORE Plant Pat. 2,082
MINIATURE ROSE PLANT
Filed Aug. 29, 1960
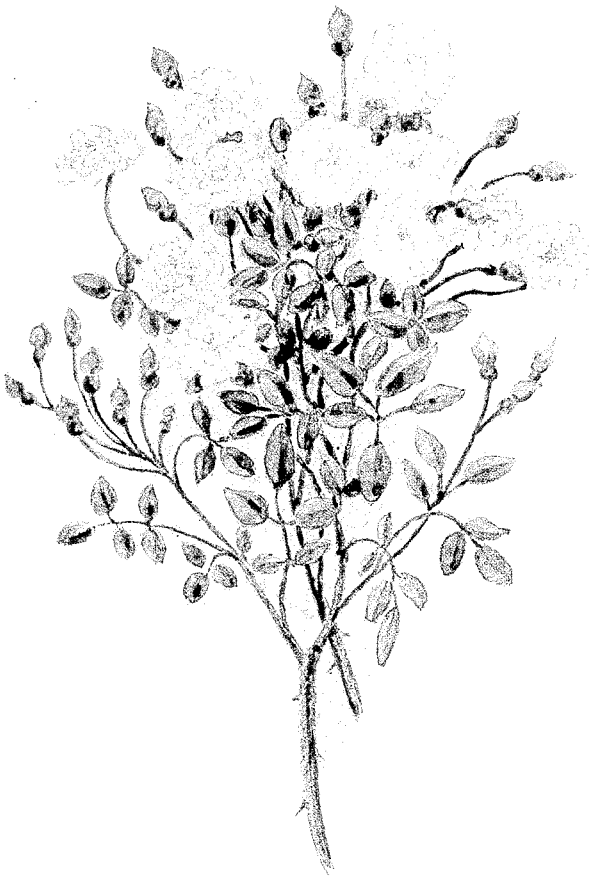
WITNESS
Addison E. Avery
INVENTOR
Ralph S. Moore
Webster & Webster
ATTYS.

United States Patent Office

Plant Pat. 2,082
Patented Aug. 29, 1961

2,082
MINIATURE ROSE PLANT

Ralph S. Moore, Visalia, Calif.

Filed Aug. 29, 1960, Ser. No. 52,753
1 Claim. (Cl. 47—61)

This invention relates to a new and distinct variety of hybrid miniature rose plant of hardy, dwarf, bush type.

The present variety is characterized—as to novelty—by a hardy, much branched but very compact plant averaging 12 inches in height and breadth, and—although the twigs and foliage are very tiny—the plant has a fast, very bushy growing habit; by such tiny foliage being abundant and glossy; by flowers that—on the same plant—individually differ in color, and which may be soft pink, lavender-pink, white with soft pink petals, or all white; by flowers of such variant color which are produced at different times or all simultaneously on one plant and even in the same cluster; and by flowers which bloom abundantly in clusters of 3 to as many as 25, and the petals of which flowers clean themselves when spent.

The present variety of miniature rose plant was originated by me, in my nursery located as Visalia, California, and under conditions of careful control and observation, as a cross between two unnamed seedlings; the seed parent having been Rosa wichuraiana × Floradora, while the pollen parent was Violette × Zee (all unpatented).

Subsequent to origination of the variety I successfully asexually reproduced it, in my nursery located as aforesaid, by cuttings; the reproductions having run true in all respects.

The drawing illustrates a spray including foliage, buds, and flowers; the flowers as illustrated being the soft pink, lavender-pink, and white.

Referring now specifically to the new and distinct variety of miniature rose plant, the following is a detailed description thereof in outline; all major color plate identifications being—as indicated—either by reference to The British Colour Council Horticultural Colour Chart, or Maerz and Paul Dictionary of Color, except where common terms of color definition are employed.

Type: Hardy; dwarf; bush; seedling; greenhouse; outdoor; garden decoration; pot plant.

Class: Hybrid miniature.

*Flowers*

Continuity: Intermittent—continuous.

Fragrance: Slight to moderate.

Flowers borne: 3 to 25, in irregularly rounded cluster on normal, short stems.

Quantity of bloom: Abundant, outdoors. Plant may produce 100 or more flowers in a season or less.

Bud:

*Peduncle.*—Medium length; slender; erect; green; smooth.

*Before calyx breaks.*—Size—small. Form—pointed, with foliaceous appendages on the surface of the bud, and with slender foliaceous parts extending beyond the tip of the bud equal to one-half of its length. Color—green.

*As calyx breaks.*—Color—either pink or white.

*As first petal opens.*—Size—very small. Form—short; ovoid. Color—either soft pink, lavender pink, or white; all pink or lavender pink petals shading to bright yellow at base when bud is opening. Opening—buds sometimes drop before opening, especially on very young growth in the spring.

Bloom:

*Size when fully open.*—Very small, averaging ½" to ¾".

*Petalage.*—Double to very double, with from 40 to 50 petals arranged regularly. Tiny inner petals roll inwardly and around pistil.

*Form.*—At first flat and full, becoming later and at maturity loosely rolled outward.

Petals: Thin; satiny both inside and outside.

*Shape.*—Outside—obovate-lanceolate. Intermediate—lanceolate. Inside—lanceolate.

*Color.*—The flowers when open, and on the same plant, individually differ in color as follows: Soft pink (1–D–1 Maerz and Paul), shading slightly darker pink (1–J–1 Maerz and Paul) at the inner petals. Lavender-pink (50–B–2 Maerz and Paul, to 50–D–4 Maerz and Paul or 30/3 British Colour Council), shading to a deeper lavender-pink at the inner petals (50–H–7 Maerz and Paul or 30/2 British Colour Council). White (1–A–1 Maerz and Paul), with inner petals soft pink (Begonia 619/3 British Colour Council). All white (1–A–1, Maerz and Paul). Flowers of the foregoing variant colors are produced—one one plant—at different times, or all simultaneously and even in the same cluster; such variance in color occurring in all weather. On newly opened flowers having soft pink or lavender-pink petals there is a shade of yellow at the base, while on fully open flowers such petals have a shade of white or near white at the base. All flowers have a very small yellow center.

*Behavior.*—Drop off cleanly.

*Flower longevity.*—Bush in garden (July)—three to four days. Cut flowers kept at living room temperatures (July)—two to three days.

Reproductive organs:

*Stamens.*—Few; arranged irregularly; mixed with petaloids.

*Filaments.*—Very short; greenish.

*Anthers.*—Very small; yellow.

*Pollen.*—Very sparse; yellow.

*Pistils.*—Few; very tiny.

*Styles.*—Even; very short; medium; bunched.

*Stigma.*—Greenish.

*Ovaries.*—All enclosed in calyx.

*Hips.*—None, or very rare. When existent: tiny ovoid or globular; green to reddish; smooth; walls thin.

*Sepals.*—Short; spear shaped; recurved; greenish.

*Seeds.*—Very few; small.

*Plant*

Foliage:

*Leaves.*—Compound of 5 leaflets; abundant; very small; moderately thin; glossy.

*Leaflets.*—Shape—lanceolate, with apex acute. Color: upper surface—normal green (22–L–8), with young leaves somewhat lighter (18–K–5); under surface—lighter normal green (21–K–4); all by reference to Maerz and Paul. Rachis—light; upper side—smooth, grooved; under side—sparsely thorny. Stipules—medium length; medium width; with medium length points turning out at an angle of less than 45 degrees.

Growth:

*Habit.*—Dwarf; bushy; much branched. Substantially of the same height and breadth, averaging 12" in each dimension.

*Growth.*—Free.

*Canes.*—Light.

*Main stems.*—Color—green. Thorns—Linden green (19–J–1 Maerz and Paul); several; short; hooked downward, with short round base. Prickles—none. Hairs—none.

*Branches.*—Color—bright green. Thorns—several; short; hooked downward, with short base. Prickles—none. Hairs—none.

*New shoots.*—Color—bright green. Thorns—few; short; hooked downward. Prickles—none. Hairs—none.

The miniature rose plant and its flowers as herein described may vary in slight detail due to climatic and soil conditions under which the variety may be grown; the present description being of the variety as grown at Visalia, California.

The following is claimed:

A new and distinct variety of rose plant of the hybrid miniature class and hardy, dwarf, bush type, characterized by a much branched but very compact plant averaging 12 inches in height and breadth, and—although the twigs and foliage are very tiny—the plant has a fast, very bushy growing habit; by such tiny foliage being abundant and glossy; by flowers that—on the same plant—individually differ in color, and which may be soft pink, lavender-pink, white with soft pink inner petals, or all white; by flowers of such variant colors which are produced at different times or all simultaneously on one plant and even in the same cluster; and by flowers which bloom abundantly in clusters of 3 to as many as 25, and the petals of which flowers clean themselves when spent.

No references cited.